(12) United States Patent
Ritt et al.

(10) Patent No.: US 7,639,851 B2
(45) Date of Patent: *Dec. 29, 2009

(54) RELATIVE CALIBRATION FOR DOSIMETRIC DEVICES

(75) Inventors: Daniel M. Ritt, Colorado Springs, CO (US); Matthew L. Whitaker, Colorado Springs, CO (US); Arthur J. Olch, Northridge, CA (US)

(73) Assignee: Radiological Imaging Technology, Inc., Colorado Springs, CO (US)

( * ) Notice: Subject to any disclaimer, the term of this patent is extended or adjusted under 35 U.S.C. 154(b) by 931 days.

This patent is subject to a terminal disclaimer.

(21) Appl. No.: 11/181,057

(22) Filed: Jul. 14, 2005

(65) Prior Publication Data

US 2006/0159320 A1   Jul. 20, 2006

Related U.S. Application Data

(62) Division of application No. 11/039,704, filed on Jan. 20, 2005, now Pat. No. 7,024,026.

(51) Int. Cl.
*G06K 9/00* (2006.01)

(52) U.S. Cl. ........................ 382/128; 382/132

(58) Field of Classification Search ............ 382/128, 382/132; 600/437; 378/29

See application file for complete search history.

(56) References Cited

U.S. PATENT DOCUMENTS

| | | | |
|---|---|---|---|
| 5,095,217 A | 3/1992 | Attix | |
| 6,219,462 B1 | 4/2001 | Anandan et al. | |
| 6,225,622 B1 | 5/2001 | Navarro | |
| 6,298,115 B1 | 10/2001 | Nilsson | |
| 6,333,964 B1 | 12/2001 | Hobel | |
| 6,345,114 B1 | 2/2002 | Mackie et al. | |
| 6,528,803 B1 | 3/2003 | Ritt | |
| 6,542,628 B1 | 4/2003 | Muller et al. | |
| 6,563,942 B2 | 5/2003 | Takeo et al. | |
| 6,574,374 B1 | 6/2003 | Acharya | |
| 6,675,116 B1 | 1/2004 | Ritt | |
| 7,233,688 B2 * | 6/2007 | Ritt et al. ............... 382/128 |
| 2002/0048393 A1 | 4/2002 | Oosawa | |
| 2002/0106054 A1 | 8/2002 | Caflisch et al. | |

FOREIGN PATENT DOCUMENTS

WO   WO 01/43070   6/2001

OTHER PUBLICATIONS

J.M. Fitzpatrick, J.B. West, C.R. Maurer Jr., "Predicting Error in Rigid-Body Point-Based Registration," IEEE Transactions on Medical Imaging, 17(5):694-702, Oct. 1998.

(Continued)

*Primary Examiner*—Duy M Dang
(74) *Attorney, Agent, or Firm*—Rader, Fishman & Grauer PLLC

(57) ABSTRACT

Calibrating the dose response of an image acquisition device comprises comparing a first self-calibration curve to a second self-calibration curve to determine the relationship between the curves; modifying an acquired image based on the at least one difference; and applying an initial calibration to the acquired image, whereby the dose response of the image acquisition device is calibrated.

17 Claims, 19 Drawing Sheets

OTHER PUBLICATIONS

ACR Bulletin, "New Intensity-modulated Radiation Therapy Codes for Hospital Outpatient Procedures," Apr. 2001, vol. 57, Issue 4, pp. 4-5,10.

International Search Report of International App. No. PCT/US 01/29327.

Oldham et al.; "Improving Calibration Accuracy in Gel Dosimetry;" Phys. Med. Biol., vol. 43 (1998), pp. 2709-2720.

Maryanski M.J. et al.; "Radiation Therapy Dosimetry Using Magnetic Resonance Imaging of Polymer Gels," Med. Phys. vol. 23, No. 5, May 1, 1996, pp. 699-705.

Oldham et al., "An Investigation into the Dosimetry of a Nine-Field Tomotherapy Irradiation Using BANG-gel Dosimetry," Phys. Med. Biol., vol. 43 (1998), pp. 1113-1132.

Williamson et al.; "Film Dosimetry of Megavoltage Photon Beams: A Practical Method of Isodensity-to-Isodose Curve Conversion," Med. Phys., vol. 8, No. 1, Jan./Feb. 1981, pp. 94-98.

Kepka et al,; "A Solid-State Video film Dosimetry System," Phys. Med. Biol., vol. 28, No. 4, (1983), pp. 421-426.

Yunping Zhu et al.; "Portal Dosimetry Using a Liquid Ion chamber Matrix: Dose Response Studies," Med Phys., vol. 22, No. 7, Jul. 1995, pp. 1101-1106.

Munro P. et al.; "X-ray Quantum Limited Portal Imaging Using Amorphous Silicon Flat-Panel Arrays," Med. Phys., vol. 25, No. 5, May 1998, pp. 689-702.

D.A. Low, W.B. Harms, S. Mutic and J.A. Purdy, "A Technique For The Quantitative Evaluation of Dose Distribuitons"; Med. Phys. 25, 656-661 (May 1998).

Nathan L. Childress and Isaac I. Rosen, The Design and Testing of Novel Clinical Parameters for Dose Comparison, Int. J. Radiation Oncology Biology Physics, vol. 56, No. 5, pp. 1464-1479 (2003).

J. Van Dyk et al., "Commissioning and Quality Assurance of Treatment Planning Computers"; International Journal of Radiation Oncology Biology Physics, vol. 26, No. 2, pp. 261-271 (1993).

Chester R. Ramsey and Daniel Chase, Clinical Implementationof IMRT in a Community Setting (2002; published by Radiation Physics Specialists of Knoxville, Tennessee).

D.A. Low, et al. "Evaluation of the gamma dose distribution comparison method" Med. Phys. 30, 2455-2464 (Sep. 2003).

Ton J. et al: "Registering Landsat Images By Point Matching" IEEE Transactions on Geoscience and Remote Sensing, IEEE Service Center, Piscataway, NJ, US, vol. 27, No. 5 Sep. 1, 1989, pp. 642-648, XP000053188, ISSN: 0196-2892.

Tretiak O. et al. "Geometric signal processing and applications to brain mapping" Acoustics, Speech, and Signal Processing, 1995. ICASSP-95., 1995 International Conference on Detroit, MI, USA May 9-12, 1995, New York, NY, USA, IEEE, US, vol. 5, May 9, 1995, pp. 2915-2918, XP010151954, ISBN: 0-7803-2431-5.

International Search Report (extended European search ) EP 05 02 6777 dated Jun. 26, 2006 (4 pages).

Childress N. et al. "Rapid radiographic film calibration for IMRT verification using automated MLC fields" Med. Phys. AIP, Melville, NY, US, vol. 29, No. 10, Oct. 2002, pp. 2384-2390, XP012011627, ISSN: 0094-2405.

Low D. A. et al: "Towards automated quality assurance for intensity modulated radiation therapy: film densitometry" proceedings of the $22^{nd}$ annual international conference of the IEEE engineering in medicine and biology society (CAT. No. 00CH37143) IEEE Piscataway, NJ, USA, vol. 1, 2000, pp. 184-187 vol. 1, XP002378228.

Low D. A. et al: "Toward automated quality assurance for intensity-modulated radiation therapy" International Journal of Radiation Oncology Biology Physics Elsevier USA, vol. 53, No. 2, Jun. 1, 2002, pp. 443-452, XP002378229, ISSN: 0360-3016.

International Search Report (extended European search) EP 06 00 0795 dated Apr. 25, 2006 (4 pages).

Non-Final Office Action dated Apr. 29, 2009 in U.S. Appl. No. 11/333,128. (12 pages).

Response to Non-Final Office Action dated Apr. 29, 2009 in U.S. Appl. No. 11/333,128. (10 pages).

Final Office Action dated Sep. 21, 2009 in U.S. Appl. No. 11/333,128. (9 pages).

Response to Final Office Action dated Sep. 21, 2009 in U.S. Appl. No. 11/333,128. (8 pages).

* cited by examiner

Initial Calibration Process

Subsequent Calibration Process

RELATIVE CALIBRATION FOR DOSIMETRIC DEVICES

RELATED APPLICATIONS

This application is a divisional of the application for Ser. No. 11/039,704, now U.S. Pat. No. 7,024,026, filed Jan. 20, 2005. This application is also related to the application for U.S. Pat. No. 6,934,653, filed May 27, 2003, entitled "SYSTEM OR METHOD FOR CALIBRATING A RADIATION DETECTION MEDIUM", which is a continuation of the application for U.S. Pat. No. 6,675,116, filed Jun. 1, 2001, claiming priority to U.S. provisional applications 60/234,745, filed Sep. 22, 2000, and 60/252,705, filed Nov. 22, 2000. This application is also related to the application for U.S. Pat. No. 6,528,803, filed Jan. 21, 2000. This application is also related to the application for U.S. Pat. No. 7,327,902, filed Dec. 10, 2004, entitled "OPTIMIZING IMAGE ALIGNMENT" and the application for U.S. patent application Ser. No. 6,937,751, filed Jul. 30, 2003 entitled "SYSTEM AND METHOD FOR ALIGNING IMAGES". All of the foregoing applications are fully incorporated herein by reference.

FIELD

The present invention relates to radiation dosimetry, and more particularly to methods and devices for efficiently performing radiation dose calibrations associated with radiotherapy.

BACKGROUND

An important use of radiotherapy, and in particular intensity-modulated radiation therapy (IMRT), is the destruction of tumor cells. In the case of ionizing radiation, tumor destruction depends on the "absorbed dose", i.e., the amount of energy deposited within a tissue mass. Radiation physicists normally express the absorbed dose in cGy units or centigray. One cGy equals 0.01 J/kg.

Radiation dosimetry generally describes methods to measure or predict the absorbed dose in various tissues of a patient undergoing radiotherapy. Accuracy in predicting and measuring absorbed dose is key to effective treatment and prevention of complications due to over or under exposure to radiation. Many methods exist for measuring and predicting absorbed dose, but most rely on developing a calibration—a curve, lookup table, equation, etc.—that relates the response of a detection medium to the absorbed dose. Useful detection media are known to those skilled in the art and include radiation-sensitive films and three-dimensional gels (e.g., 'BANG' and 'BANANA' gels) which darken or change color upon exposure to radiation. Other useful detection media include electronic portal-imaging devices, Computed Radiography (CR) devices, Digital Radiography (DR) devices, and amorphous silicon detector arrays, which generate a signal in response to radiation exposure.

There are various known methods for developing a calibration curve. For example, U.S. Pat. No. 6,675,116, assigned to the assignee of the present application and fully incorporated herein by reference, discloses providing a detection medium that responds to exposure to ionizing radiation, and preparing a calibration dose response pattern by exposing predefined regions of the detection medium to different ionizing radiation dose levels. The '116 patent further discloses measuring responses of the detection medium in the predefined regions to generate a calibration that relates subsequent responses to ionizing radiation dose. Different dose levels are obtained by differentially shielding portions of the detection medium from the ionizing radiation using, for example, a multi-leaf collimator, a secondary collimator, or an attenuation block. Different dose levels can also be obtained by moving the detection medium between exposures. The '116 patent further discloses a software routine fixed on a computer-readable medium that is configured to generate a calibration that relates a response of a detection medium to an ionizing radiation dose.

Methods such as those disclosed in the '116 patent require exposing discrete portions of the detection medium to different and known amounts of radiation using a linear accelerator or similar apparatus in order to develop a calibration curve or lookup table. Typically about twelve, but often as many as twenty-five, different radiation dose levels are measured in order to generate a calibration curve or look-up table. Generally, the accuracy of the calibration increases as the number of measured radiation dose levels increases. However, the greater the number of measurements, the more expensive and time consuming the calibration process becomes. Thus, it would be desirable to have a system and method that provides calibration information by analyzing one "acquired image" obtained by applying a radiation therapy plan to a quality assurance device and capturing the radiation intensity distribution.

Methods of correcting an acquired image so that a dosimetry acquisition system that has been once calibrated will not have to be recalibrated each time are known. For example, U.S. Pat. No. 6,528,803, assigned to the assignee of the present application and fully incorporated herein by reference, teaches exposing portions of test films to an array of standard light sources to obtain an optical density step gradient, which can then be compared to a corresponding optical density step gradient on one or all of a set of calibration films. However, existing methods such as those disclosed by the '803 patent require additional equipment and time to gather data relating to the optical density step gradient. In some cases, it would be desirable to have a system and method providing calibration information for a subsequent acquired image that did not require extra equipment and that took a minimum amount of time even if this was only a "relative" calibration (expressed in percent) and not an "absolute" calibration (in dose and trace able to a national standard).

Further, it may also be desirable to have a system to evaluate the ability of experimentally derived calibration curves to model the dose distributions produced by a systems that create treatment plans, and other predictions of dose distribution, in order to determine where differences occur by modeling inaccuracies as opposed to true experimental differences.

BRIEF SUMMARY

According to an embodiment, a system for calibrating the dose response of an image acquisition device comprises means for creating a dose map that indicates dosages that are included in a treatment plan, means for creating an acquired image that includes representations of dosage intensities recorded from an application of the treatment plan; and means for creating a self-calibration curve that relates the dosages to the dosage intensities.

Further, according to an embodiment, a system for calibrating the dose response of an image acquisition device comprises a first self-calibration curve, a second self-calibration curve, an initial calibration; and means for performing computations including: (1) determining at least one difference or fit between the first self-calibration curve and the second self-calibration curve, (2) modifying an acquired image based on the at least one difference or fit; and (3) producing a relative calibration based on an application of the initial calibration to the acquired image.

Further, according to an embodiment, a method for calibrating the dose response of an image acquisition device comprises comparing a first self-calibration curve to a second self-calibration curve to determine the relationship between the curves; modifying an acquired image based on the at least one difference; and applying an initial calibration to the acquired image, whereby the dose response of the image acquisition device is calibrated.

DETAILED DESCRIPTION

A calibration is developed for a first treatment plan that relates planned dosages to a detection medium's response to an absorbed dose. Also, an IMRT self calibration curve ("ISCC" or "ISCC curve"), relating dosage intensities in the first treatment plan to pixel intensities on an acquired image, is developed relating to the first treatment plan. An ISCC curve is then developed for a second treatment plan. A comparison of the ISCC curve relating to the first treatment plan with the ISCC curve relating to the second treatment plan allows adjustment of an acquired image relating to the second treatment plan so that the calibration may be used to provide calibration information with respect to the second treatment plan. Accordingly, the systems and methods disclosed herein provide for simple, quick, efficient, and inexpensive calibrations of image acquisition devices used to acquire test images before a treatment plan is applied to a patient.

Figure 1:
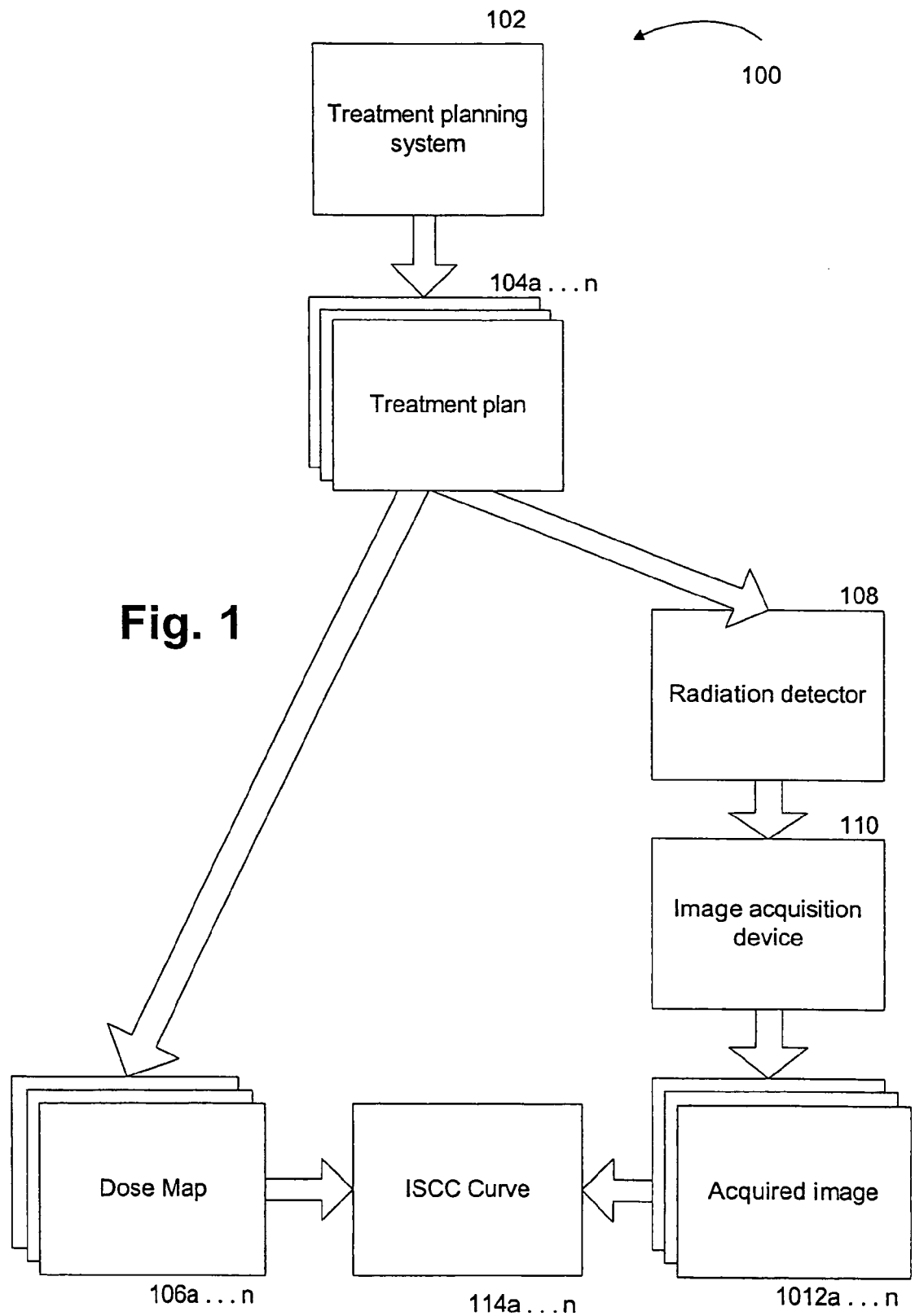
FIG. 1 is a block diagram providing an overview of a system used in at least one embodiment to build an IMRT self calibration curve (ISCC).

The use of the various components of system 100 shown in FIG. 1 is described in detail below. In general, a treatment plan may be applied to a radiation detector, and thereby recorded on some medium or device, producing acquired image 112, such as is shown and described more fully with reference to FIG. 1 below. Acquired image 112 is compared to a dose map 106, also described more fully with reference to FIG. 1 below, that represents the intensity of dosages planned as part of a treatment.

System Overview

FIG. 1 provides an overview of a system 100 used in at least one embodiment to build an IMRT self calibration curve (ISCC). Treatment planning system 102 is any of a variety of treatment planning systems known to those skilled in the art, including but not limited to the Pinnacle 3 system manufactured by Phillips Medical Systems of Andover, Mass.; BrainSCAN, manufactured by Brainlab AG of Heimstetten, Germany; PLATO SunRise by Nucletron of Veenendaal, The Netherlands; Eclipse, manufactured by Varian Medical Systems of Palo Alto, Calif.

Figure 6A:
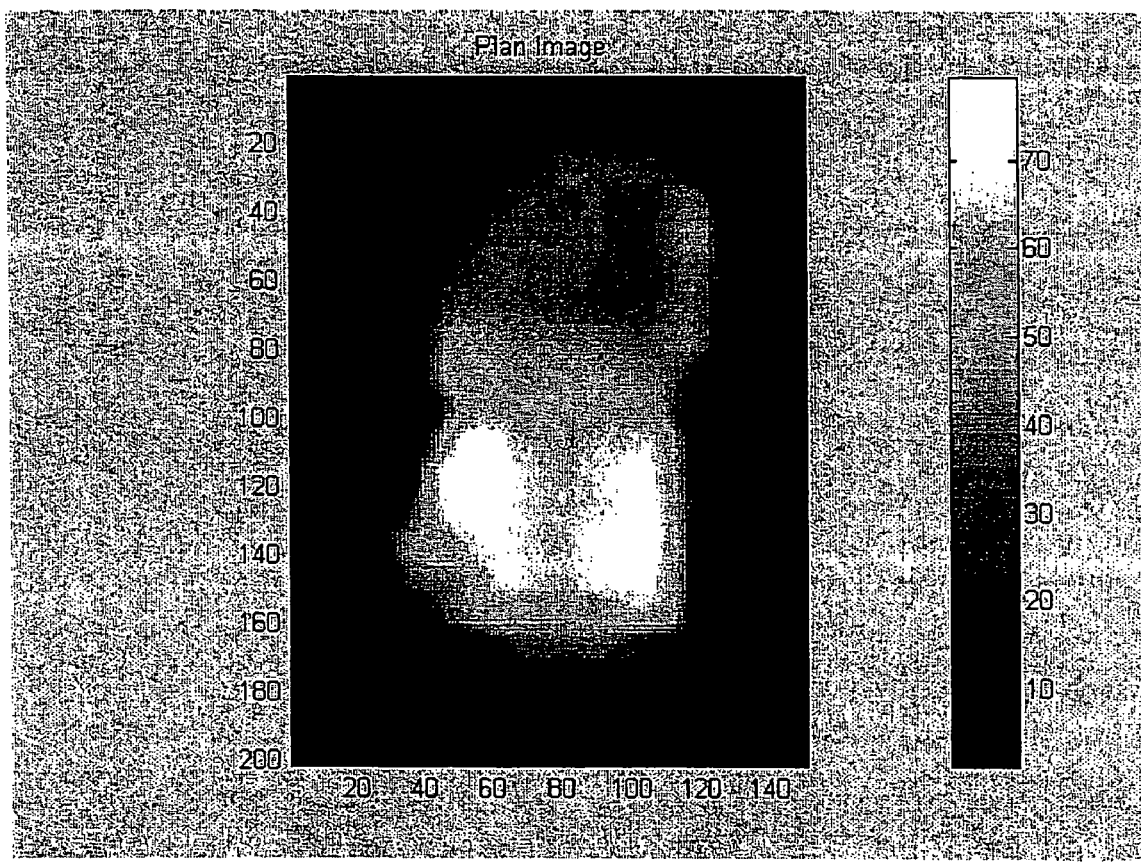
FIG. 6A shows an example of a dose map.

Treatment planning system 102 is used to create one or more radiation treatment plans 104. Treatment planning system 102 is also used to create dose map 106, sometimes also referred to as the plan image. Such use of treatment planning system 102 will be well known to those skilled in the art. Further, those skilled in the art will recognize that dose map 106 shows the expected distribution of the planned radiation dose in a quality assurance phantom or a patient. An example of a dose map 106 is shown in FIG. 6A.

Radiation detector 108 is a device capable of detecting and receiving radiation such as will be known to those skilled in the art. In some embodiments, radiation detector 108 is a quality assurance phantom, also known as a test phantom, such as will be known to those skilled in the art. The purpose of the test phantom is to emulate a medium that is to receive a dose of radiation, such as human tissue.

Figure 6B:
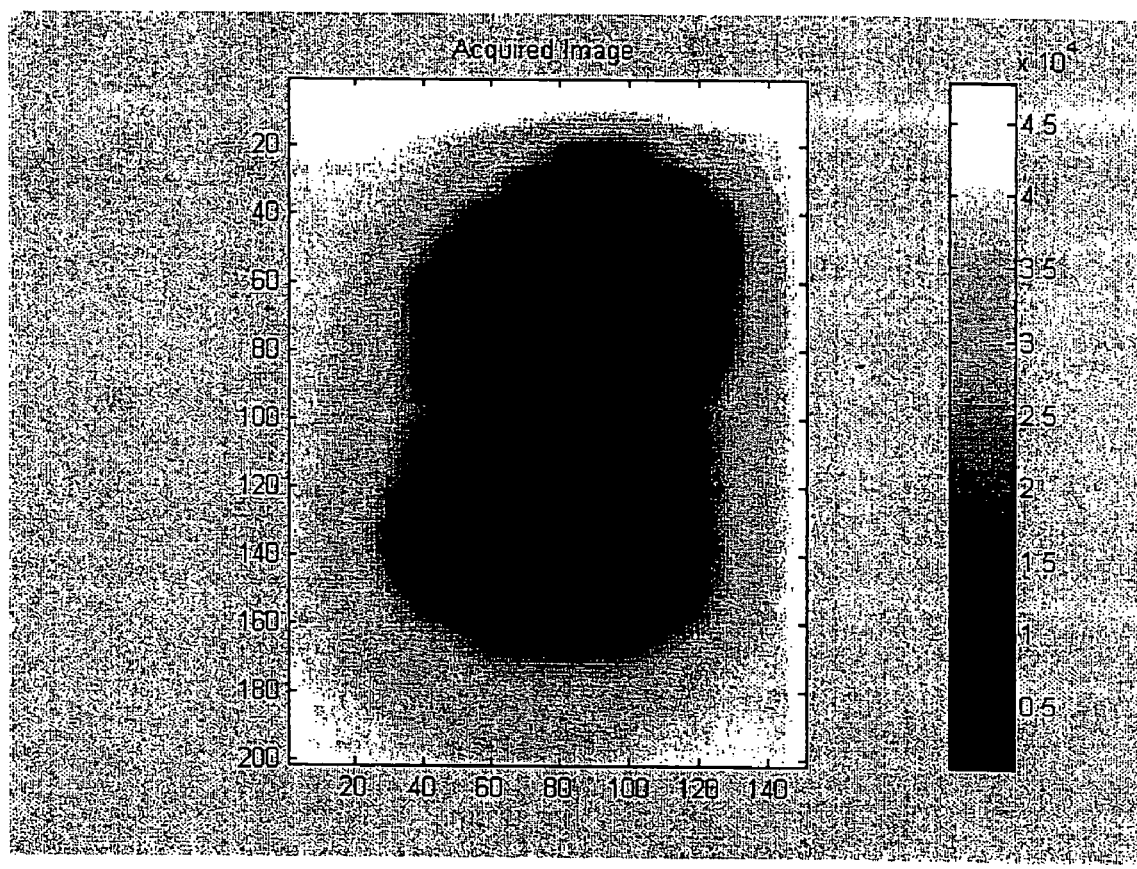
FIG. 6B shows an example of an acquired image.

Image acquisition device 110 may be any such device or medium as will be known to those skilled in the art for recording detected radiation, including, but not limited to, radiographic film, a computed radiography device, an electronic portal imaging device, a charge-coupled device (CCD) camera, or BANG gel. Image acquisition device 110 produces one or more acquired images 112. As described below, an acquired image 112 and dose map 106 are used to create ISCC curve 114. An example of an acquired image 112 is shown in FIG. 6B. As further described below, most embodiments will create at least two ISCC curves 114 relating to at least two treatment plans 104.

Those skilled in the art will recognize that the processes described herein with reference to system 100 may be carried out by using one or more computers such as are known to those skilled in the art and may include any device or combination of devices capable of functioning as described herein with respect to system 100, including receiving, outputting, processing, transforming, incorporating, and/or storing information. Accordingly, the processes described herein may be carried out by the execution of computer-executable instructions embodied on a computer-readable medium. For example, a computer used with system 100 may be a general purpose computer capable of running a wide variety of different software applications. Further, such a computer may be a specialized device limited to particular functions. In some embodiments, the computer is a network of computers. In general, system 100 may incorporate a wide variety of different information technology architectures. The computer is not limited to any type, number, form, or configuration of processors, memory, computer-readable mediums, peripheral devices, computing devices, and/or operating systems.

Further, some of the elements of system 100 may exist as representations within a computer. For example, treatment plan 104, dose map 106, acquired image 112, and/or ISCC curve 114 may exist as representations within one or more computers. Accordingly the computer may include or be coupled to interfaces and access devices for providing users (e.g., a radiological technician) with access to system 100. Thus, users are able to access the processes and elements of system 100 using any access devices or interfaces known to those skilled in the art.

Initial Calibration Process

Figure 2:
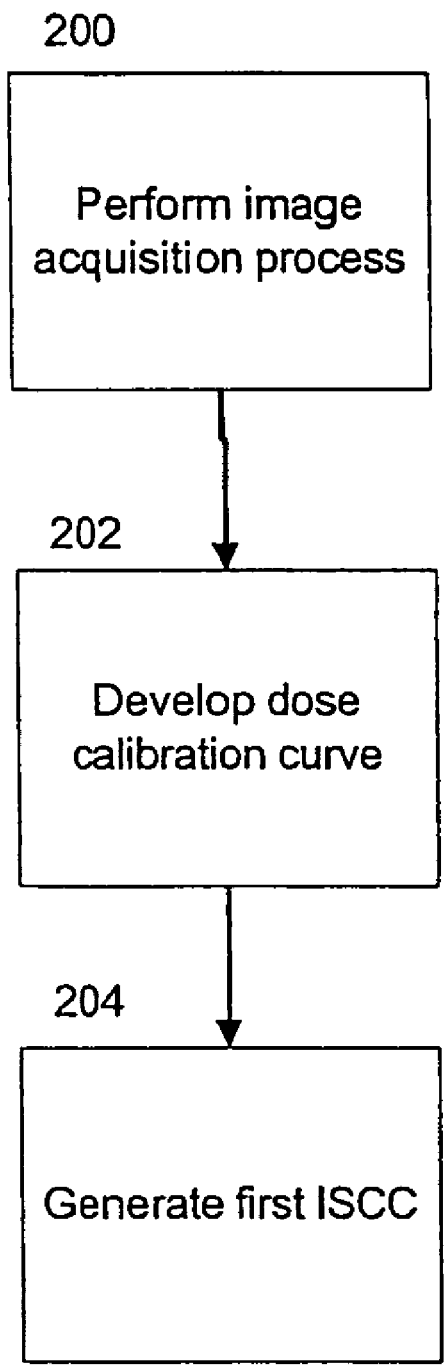
FIG. 2 is a process flow diagram describing a process flow for an initial calibration process, according to an embodiment.
Figure 3:
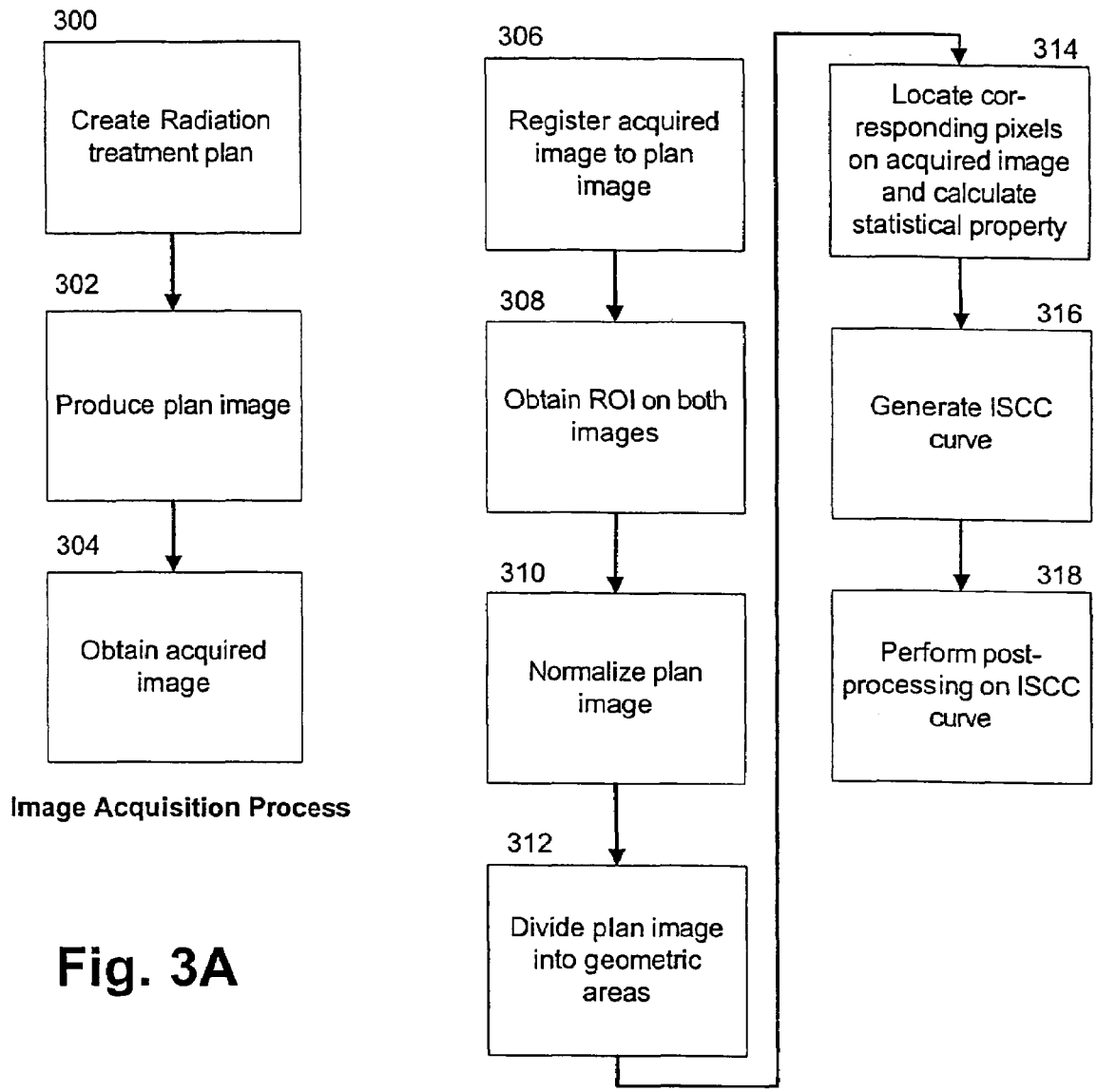
FIG. 3A is a process flow diagram describing a process of acquiring images to be used in building an ISCC curve, according to an embodiment.
FIG. 3B is a process flow diagram describing an ISCC generation process, according to an embodiment.

FIG. 2 describes a process flow for an initial calibration process. Step 200 represents the process of obtaining a first acquired image 112a representing a radiation distribution from a first radiation treatment plan 104a. The process represented in step 200 is described in detail with reference to FIG. 3A. Step 202 represents the process of developing a calibration, e.g., a calibration curve or equation, that relates the radiation intensity distribution of acquired image 112a to the radiation dose provided by the application of treatment plan 104a. As discussed above, various means, methods, and devices for performing the calibration of step 202 will be known to those skilled in the art. Step 204 represents the process of generating an ISCC curve 114a. The process represented in step 204 is described in detail with reference to FIG. 3B.

Image Acquisition Process

FIG. 3A is a flow diagram describing a process of acquiring images to be used in building an ISCC curve.

In step 300, a radiation treatment plan 104 is created. Creation of radiation treatment plans is well known, and can be accomplished using a variety of known treatment planning systems 102. As is well known, a radiation treatment plan may include the intensity, duration, and location of radiation doses that will be delivered to a tumor site during a course of radiation therapy.

In step 302, treatment planning system 102 is used to create dose map 106 associated with treatment plan 104, sometimes also referred to as a plan image.

In step 304, treatment plan 104 is applied to a radiation detector 108. The radiation distribution of the detected radiation is recorded on image acquisition device 110. Image acquisition device 110 is used to produce an acquired image 112, which represents the radiation distribution produced from the application of treatment plan 104. Those skilled in the art will recognize that acquired image 112 may be produced in a variety of ways. For instance, the example acquired image 112 shown in FIG. 6B represents the scanned digital image of a quality assurance film of an IMRT treatment field. In some embodiments acquired image 112 may be filtered, such as with a 5 by 5 median filter or some other filtering technique as may be known to those skilled in the art. Filtering may be used to reduce noise and/or to adjust for pixels or voxels of different sizes between the treatment plan and the image acquisition device.

ISCC Generation Process

Turning now to FIG. 3B, an ISCC generation process is described. Use of this ISCC generation process is discussed herein with respect to certain embodiments, but it should be understood that the process could be applied to yet other embodiments that will become apparent to those skilled in the art upon reading this disclosure. In step 306, acquired image 112 is registered to dose map 106. Registering images refers to the process of aligning images so that they occupy the same image space, and can then be compared and/or combined. Various methods and devices for registering images will be known to those skilled in the art, some of which are discussed in co-pending U.S. application Ser. No. 10/630,015 and U.S. application Ser. No. 11/009,602, filed Dec. 10, 2004, entitled "OPTIMIZING IMAGE ALIGNMENT".

In step 308, a common region of interest (ROI) is obtained with respect to dose map 106 and acquired image 112. The common ROI can be no larger than the smaller of dose map 106 and acquired image 112, and is chosen to exclude any extraneous non-dose related markings on acquired image 112. For example, the ROI should not include any writing or fiducial markings, and should not include any areas that are off the edges of dose map 106 or acquired image 112.

As part of step 308, various automated techniques known to those skilled in the art may be employed to exclude anomalous small areas of dose map 106 and acquired image 112, such as areas where one image contains pinpricks. Further, various known thresholding techniques may be employed to exclude areas in selected dose ranges that are suspected of having poor correlation. These might include low dose areas, high gradient areas, area close to physical media boundaries, etc.

In step 310, pixel values in dose map 106 are normalized to the maximum value of a pixel in dose map 106, and then are converted to percentage values if a "relative" measurement instead of an "absolute" measurement is desired.

Figure 7A:
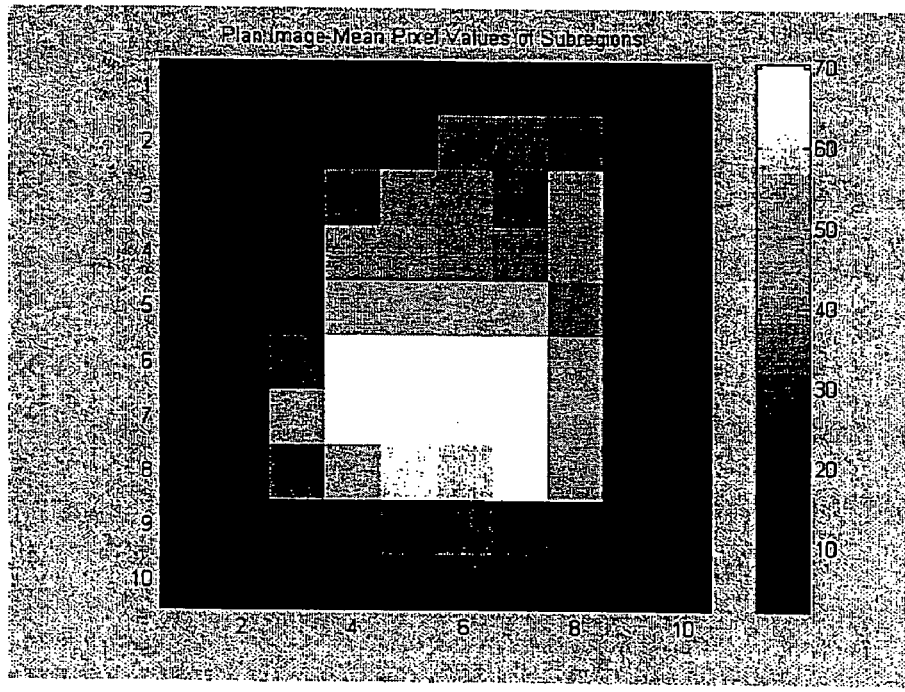
FIG. 7A shows an example of a dose map divided into small geometric areas and after a statistical function has been applied to the areas.

In a first embodiment, at step 312 dose map 106 is divided into small geometric areas. An example of a dose map 106 divided into small geometric areas (and after a statistical function has been applied to the areas, as described below) is shown in FIG. 7A. In one embodiment, the geometric areas are rectangles (or cubes for 3D images) that each include one percent of the area of the dose map 106. It should be noted that the geometric areas of the image may or may not be contiguous and may or may not physically overlap depending on the specific images employed.

In a second embodiment, at step 312 the dose levels on dose map 106 are divided into dose ranges. These dose ranges may or may not be contiguous and may or may not overlap. In one embodiment each dose range covers 1% of the total dose range on the plan image. That is, each 1% increment covers the range from 0 to the maximum dose on dose map 106 on a scale of 0 to 100. For each range of pixels in the dose curve a statistical measure such as the mean or the median is calculated. That is, the process finds all the pixels in each dose range on the plan image, i.e., dose map 106, and takes the mean (or median or some other measure of central tendency) of those pixels. An index locating the pixels on the registered images in each range is maintained.

Figure 9A:
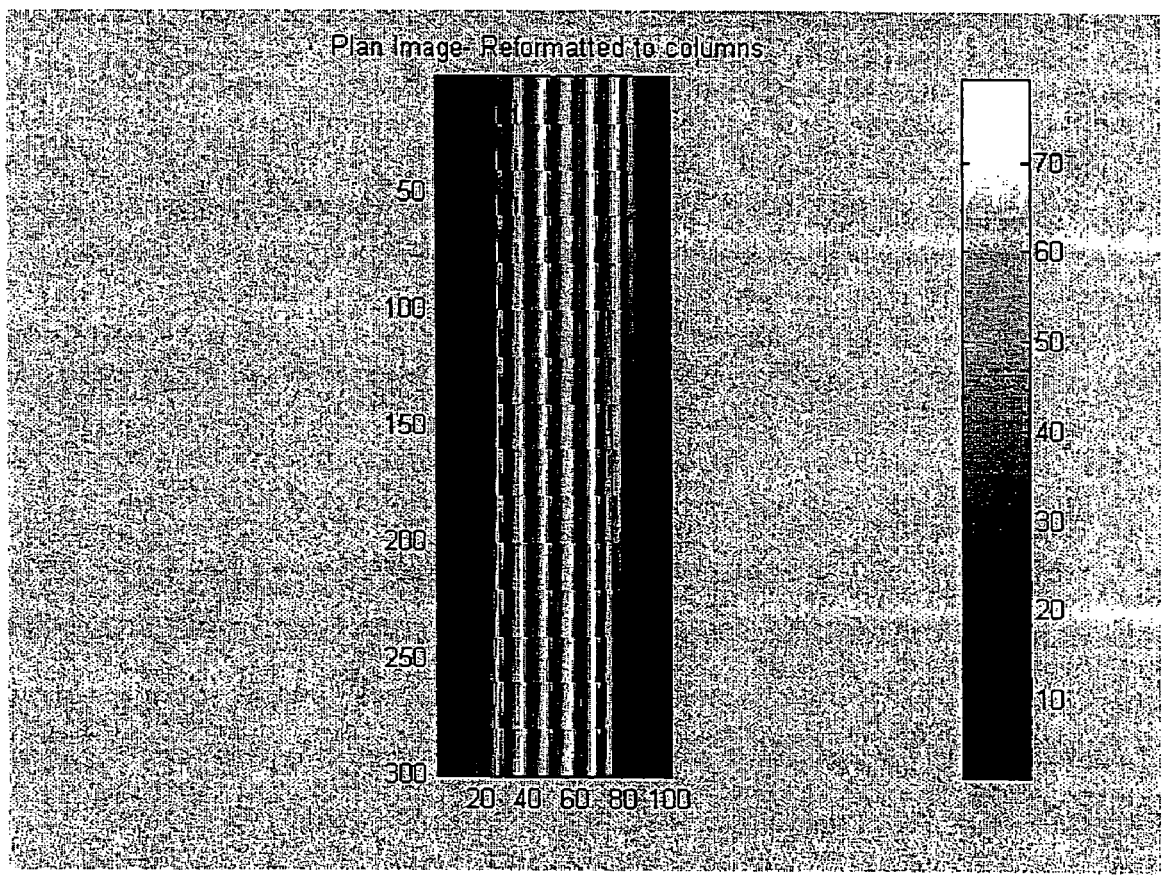
FIG. 9A shows an example of a dose map in column format.

In yet a third embodiment, at step 312, dose map 106 is divided into sub-regions such as the geometric areas described above comprising a percentage of the area of dose map 106. Dose map 106 is then translated into what is referred to as "column format." It should be understood that use of column format is optionally employed for the sake of simplifying the process but that steps 312 and the steps following step 312 could be practiced without representing dose map 106 and acquired image 112 in column format. An example of a dose map 106 in column format is shown in FIG. 9A. Individual sub-regions of the dose map 106 shown in FIG. 6A are represented in individual columns of the image shown in FIG. 9A.

Figure 7B:
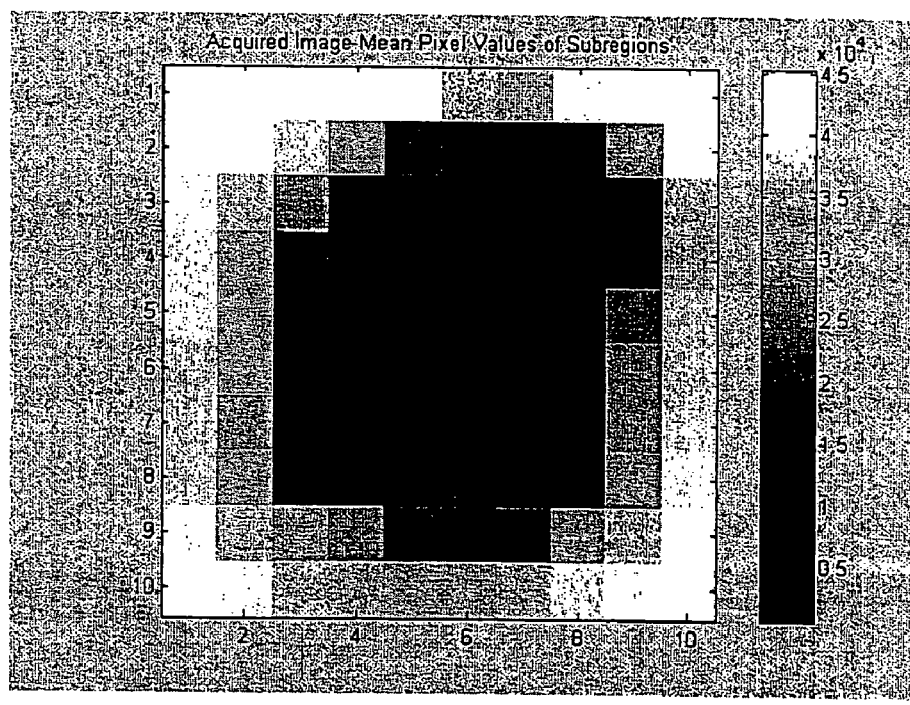
FIG. 7B shows an example of an acquired image divided into small geometric areas and after a statistical function has been applied to the areas.

In the first embodiment discussed with reference to step 312, at step 314 pixels are located on the acquired image 112 that correspond to each geometric area of dose map 106, defined as described above with respect to step 312. Dose map 106 and acquired image 112 may optionally be trimmed before corresponding pixels are located so that each of dose map 106 and acquired image 112 have an area that is a whole number multiple of each geometric area. An acquired image 112 divided into geometric areas is shown in FIG. 7B. For each set of pixels so located, some statistical measure or property is calculated. In some embodiments, for example, those depicted in FIGS. 7A and 7B, the mean value of the pixel intensity is calculated for each set of located pixels. Other embodiments may calculate the median or some other statistical property such as will be known to those skilled in the art. For example, median values preserve edges in images, while averaging tends to smooth the edges. The selection of the statistical property may depend on several factors which may include how fast the dose changes within a region.

At step 314, in the second embodiment discussed with reference to step 312, pixels are located in the acquired image 112 corresponding to dose ranges identified in dose map 106 as described above with respect to step 312. A statistical measure (e.g., mean, median etc.) of each dose range in the acquired image 112 is then taken as described above with respect to dose map 106 in step 312.

Figure 9B:
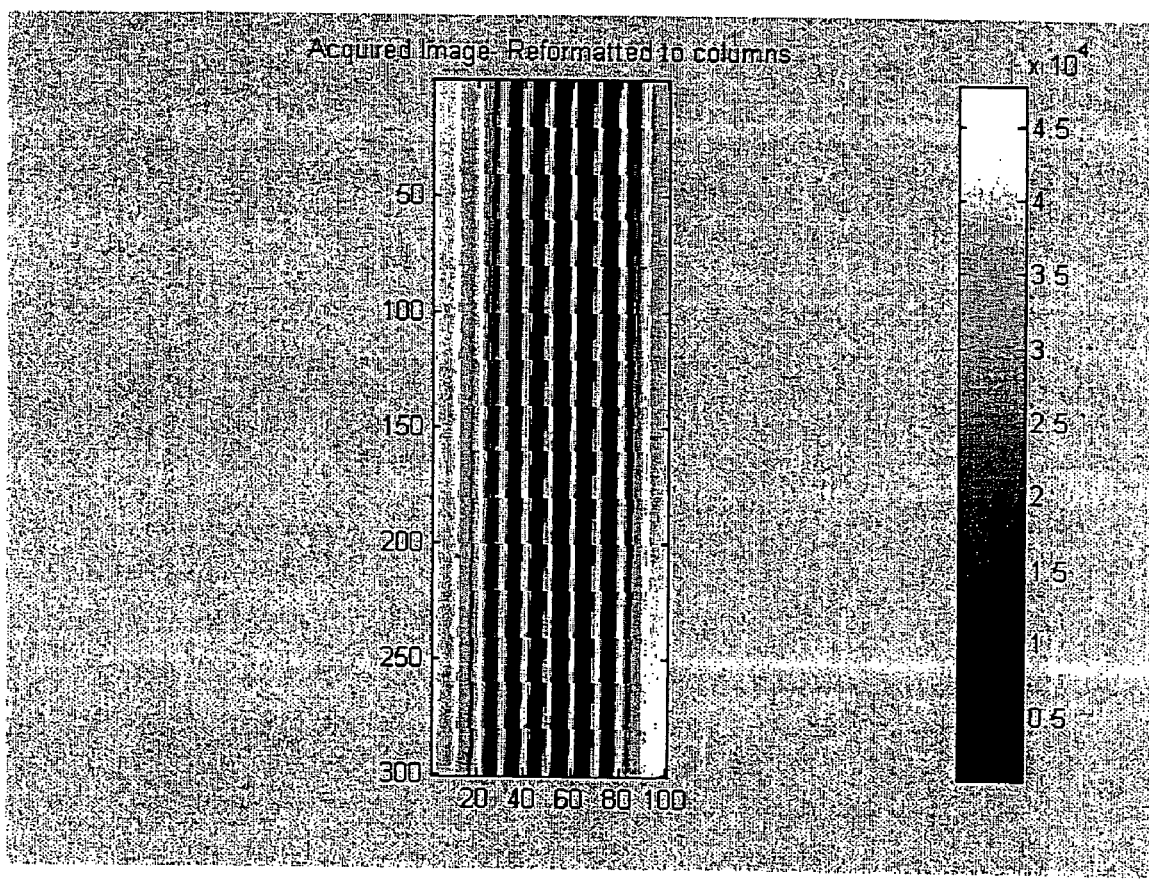
FIG. 9B shows an example of an acquired image in column format.
Figure 10:
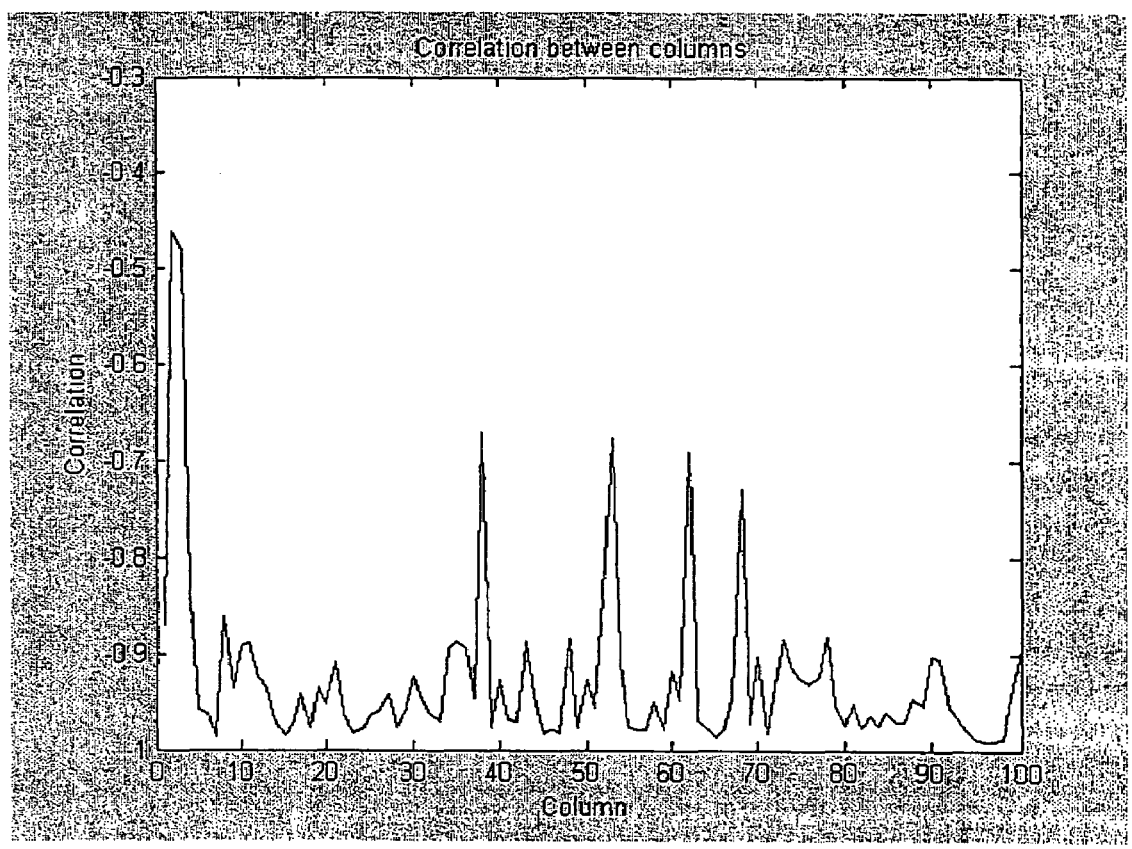
FIG. 10 shows an exemplary graph representing the correlation coefficient for each set of corresponding columns in the mages shown in FIGS. 9A and 9B
Figure 11A:
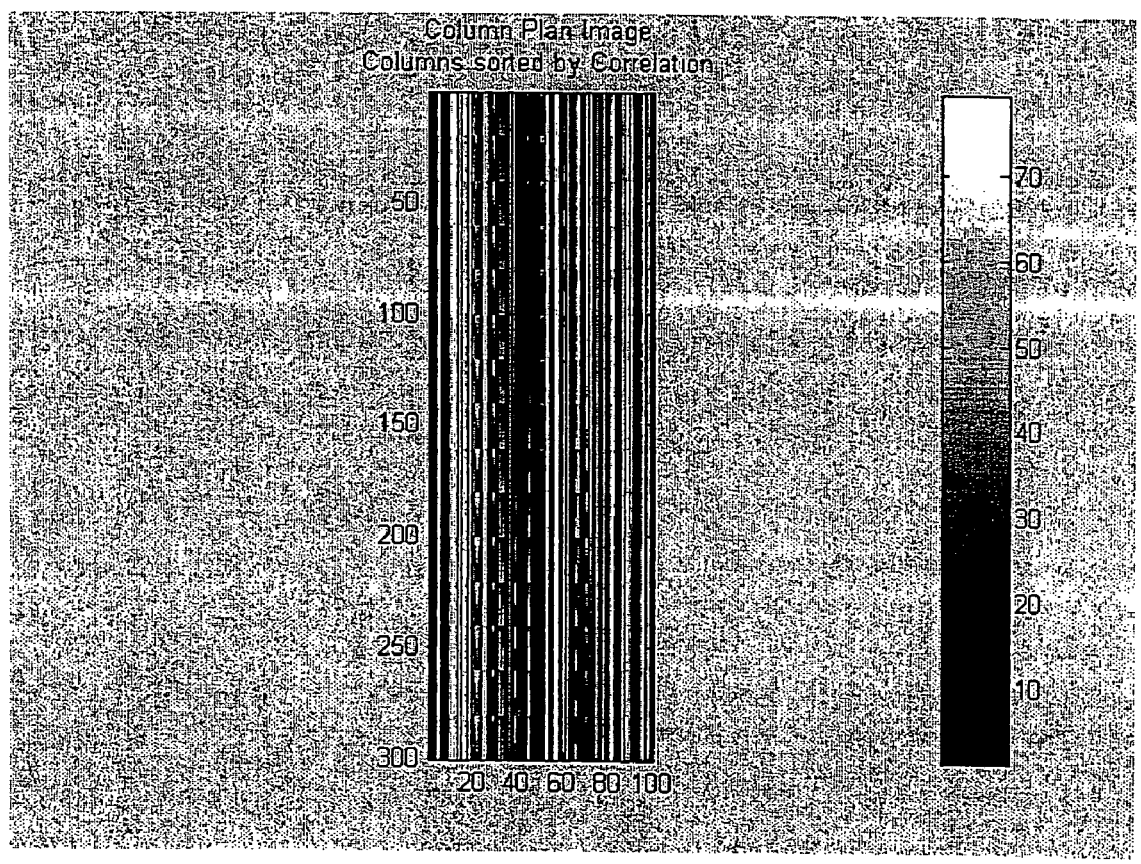
FIG. 11A shows an exemplary image in column format representing a dose map in which the columns are sorted according to the value of a correlation coefficient.
Figure 11B:
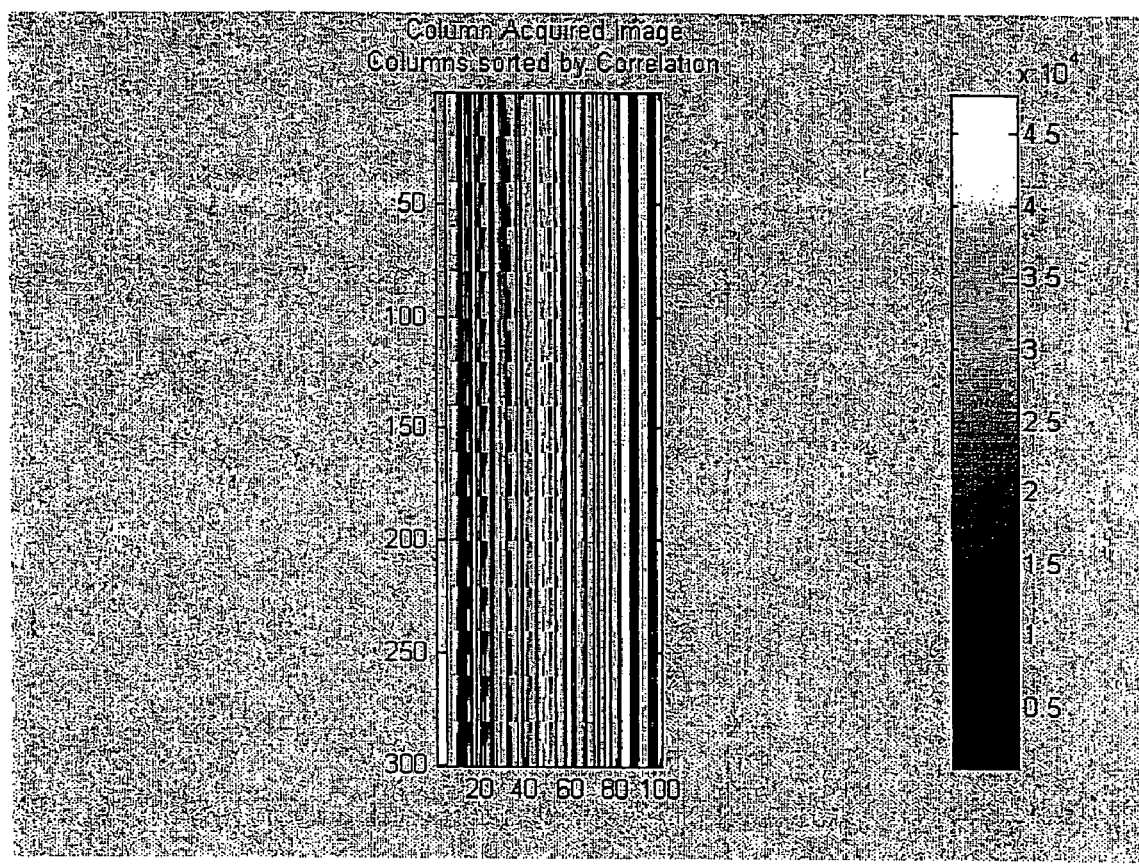
FIG. 11B shows an exemplary image in column format representing an acquired image in which the columns are sorted according to the value of a correlation coefficient.

In the third embodiment discussed above with reference to step 312, at step 314 acquired image 112 is divided into sub-regions and then represented in column format as shown in FIG. 9B. For each such sub-region a correlation is made between the pixels in the reference image, i.e., dose map 106, and the pixels in the corresponding geometric areas in the acquired image 112. Such correlations are known to those skilled in the art. For example, FIG. 10 shows a graph representing the correlation coefficient, such as will be known to those skilled in the art, for each set of corresponding columns (numbered 1 through 100) in the mages shown in FIGS. 9A and 9B. The corresponding sub-regions represented by the corresponding columns are ranked in order of the measure of correlation. FIGS. 11A and 11B show images in column format representing respectively a dose map 106 and an acquired image 112 in which the columns are sorted according to the value of a correlation coefficient. Starting with the most highly correlated areas the corresponding pixels are used to develop a calibration curve in a manner similar to that described in the preceding paragraph.

In some embodiments a correlation threshold is established such that only columns whose correlation exceeds a predetermined threshold are considered when building an ISCC curve. For example, with reference to FIGS. 11A and 11B, columns 1-33 of the column images have correlations less than or equal to −0.97, the value −0.97 having been selected as the correlation threshold. Accordingly, in this example, only columns 1-33 are to be considered when building the ISCC curve.

Figure 4:
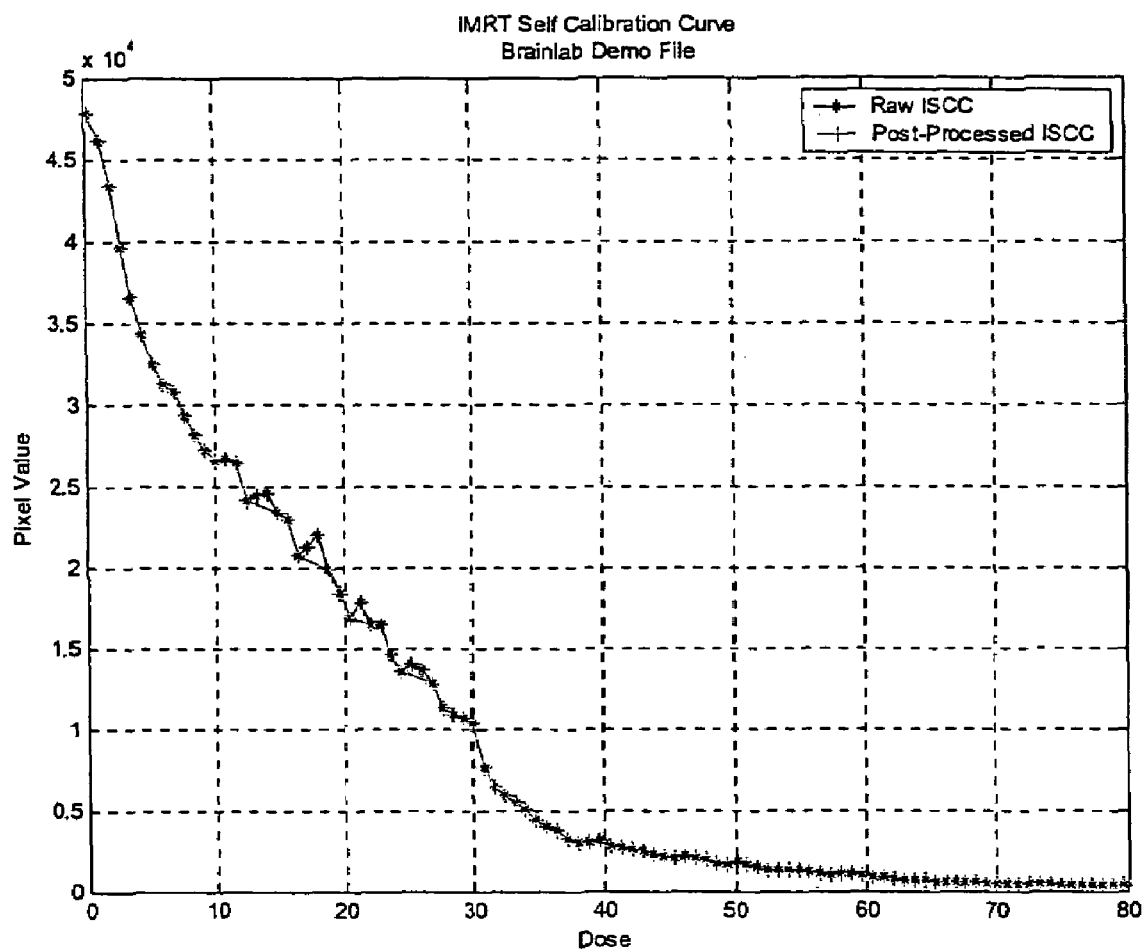
FIG. 4 shows an example of an ISCC curve.
Figure 8A:
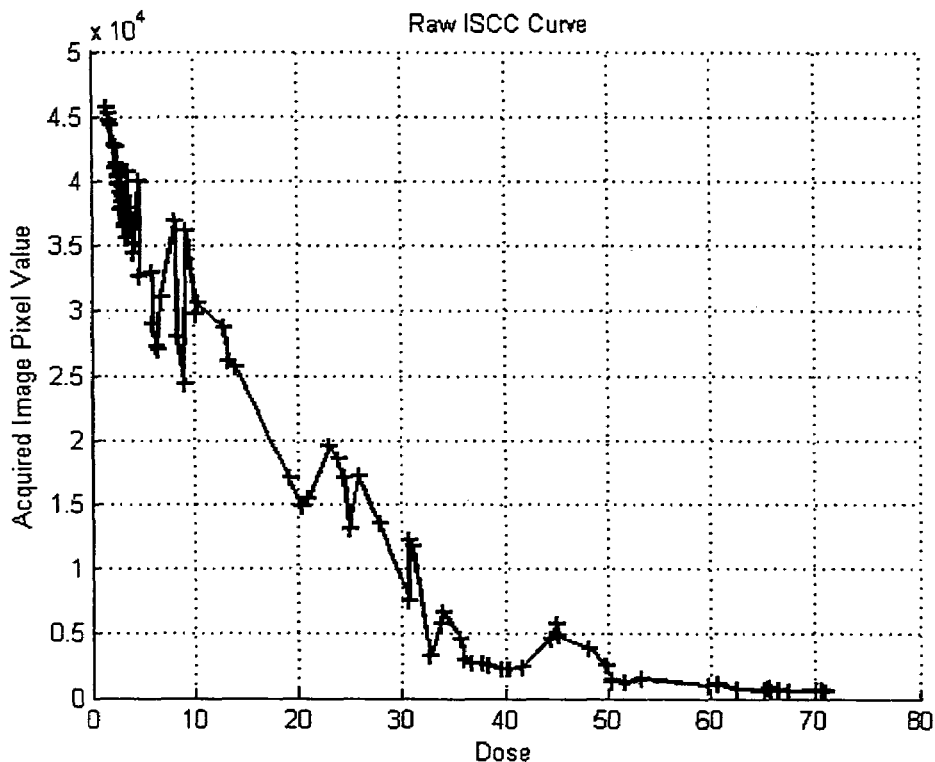
FIG. 8A shows an example of a raw ISCC curve.
Figure 12A:
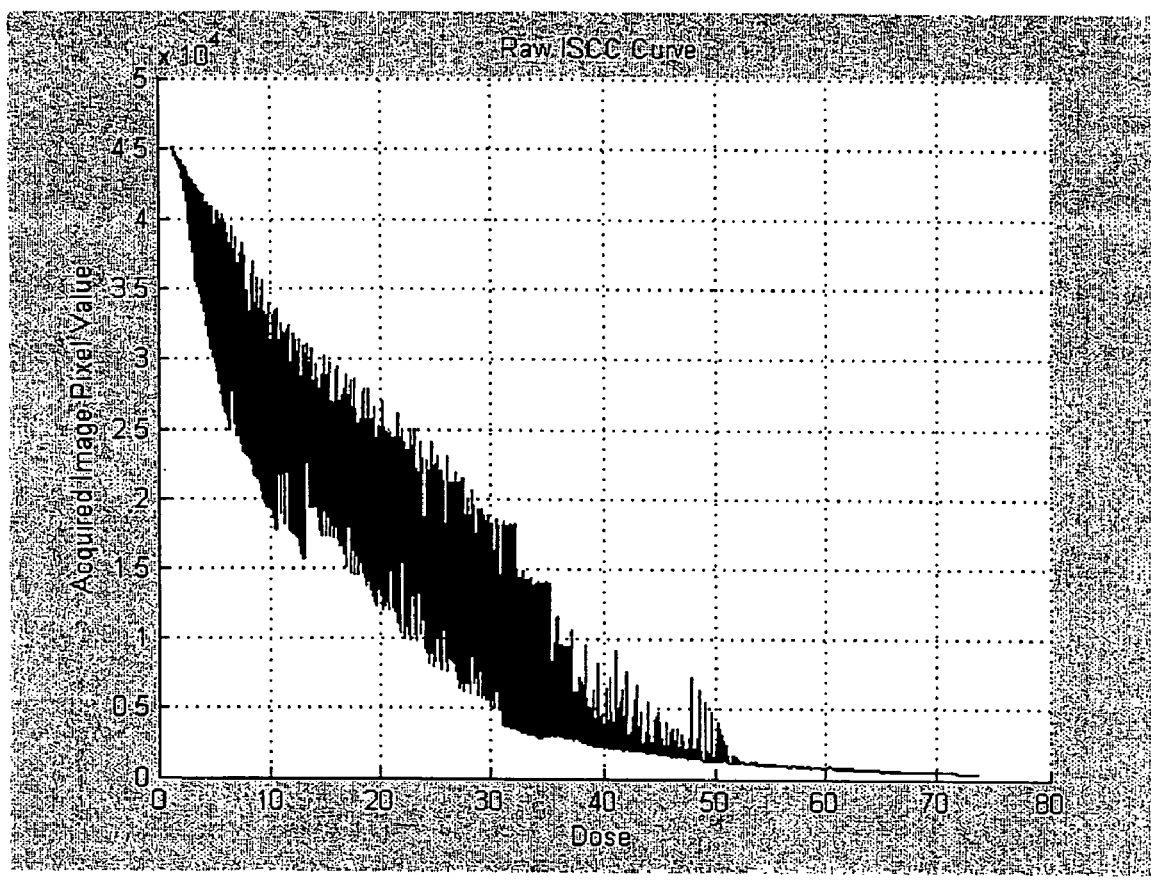
FIG. 12A shows an exemplary raw ISCC curve based on plotting pixel values for areas of a dose map and acquired image that exceed a correlation threshold

In step 316, a raw ISCC curve is developed. An example of an ISCC curve produced in one practiced embodiment is shown in FIG. 4. The ISCC curve of this embodiment plots a value representing the intensity of the dose of treatment plan 104 for each of the ranges of dose map 106 defined in step 312 against a value representing the pixel intensity in each of the corresponding pixels in the acquired image 112, this value being related to whatever statistical measure was selected in step 314. Another example of a raw ISCC curve is provided in FIG. 8A. The raw ISCC curve shown in FIG. 8A was developed by dividing the dose map 106 shown in FIGS. 6A and 7A and the acquired image shown in FIGS. 7A and 7B into small geometric areas. FIG. 12A shows a raw ISCC curve based on plotting pixel values for areas of the dose map 106 and acquired image 112 that exceed the correlation threshold discussed above with respect to step 314.

Figure 8B:
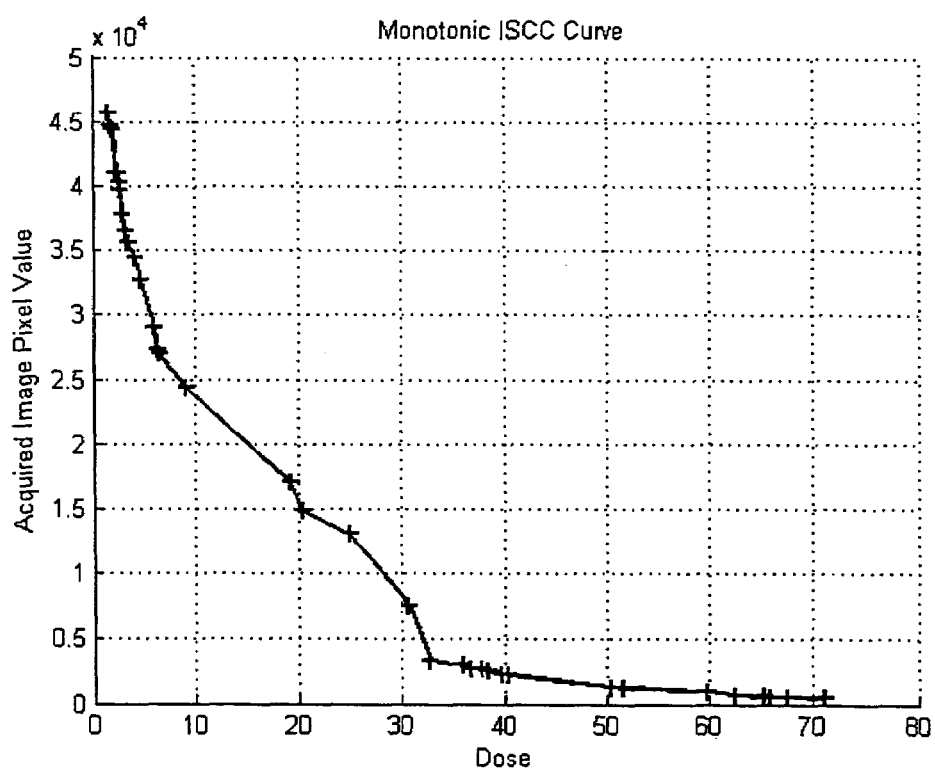
FIG. 8B shows an example of a post-processed ISCC curve.
Figure 12B:
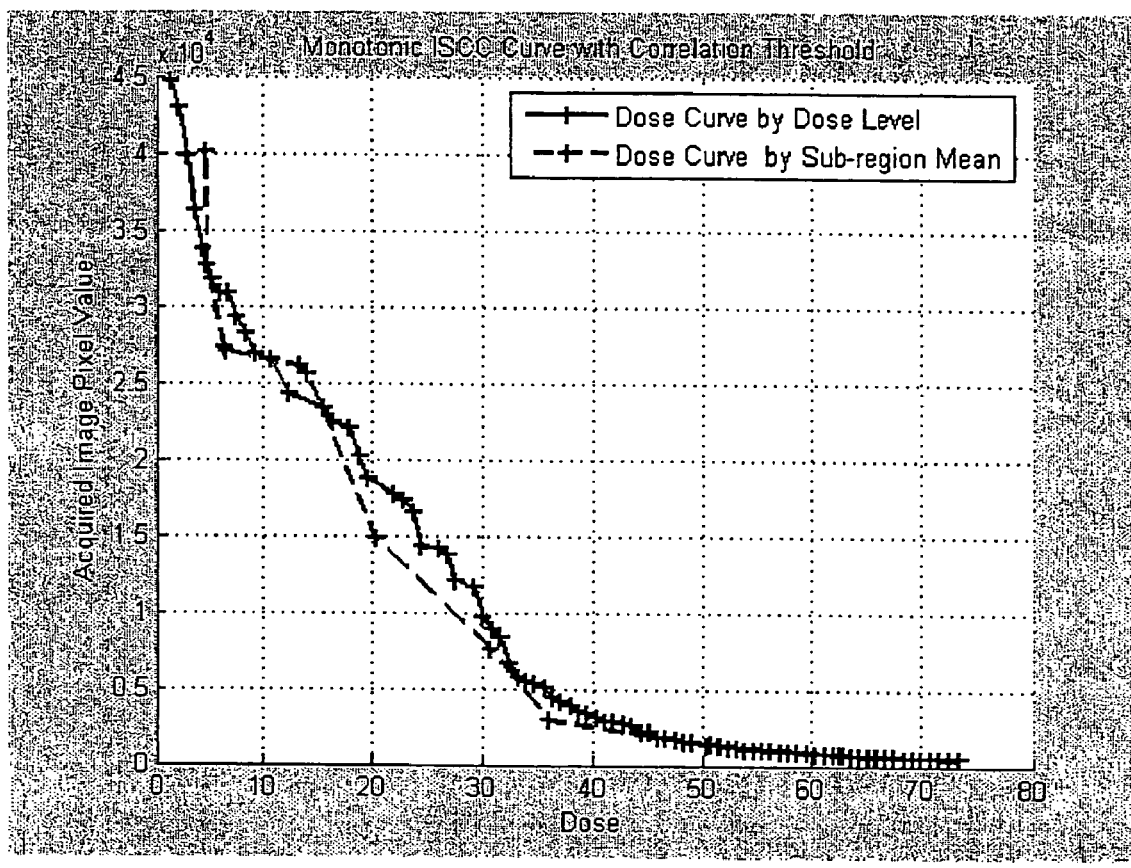
FIG. 12B shows an example of the ISCC curve of FIG. 12A after post-processing.

In step 318, the ISCC curve developed in step 318 is post-processed to ensure that pixel values monotonically decrease as dose values rise. In addition, other post-processing techniques such as will be known to those skilled in the art may be applied. For example, techniques to smooth or fit the ISCC curve may be applied in step 318. FIG. 8B shows an ISCC curve resulting from post-processing the raw ISCC curve shown in FIG. 8A. FIG. 12B shows an ISCC curve resulting from post-processing the raw ISCC curve shown in FIG. 12A.

Subsequent Calibration Process

Figure 5:
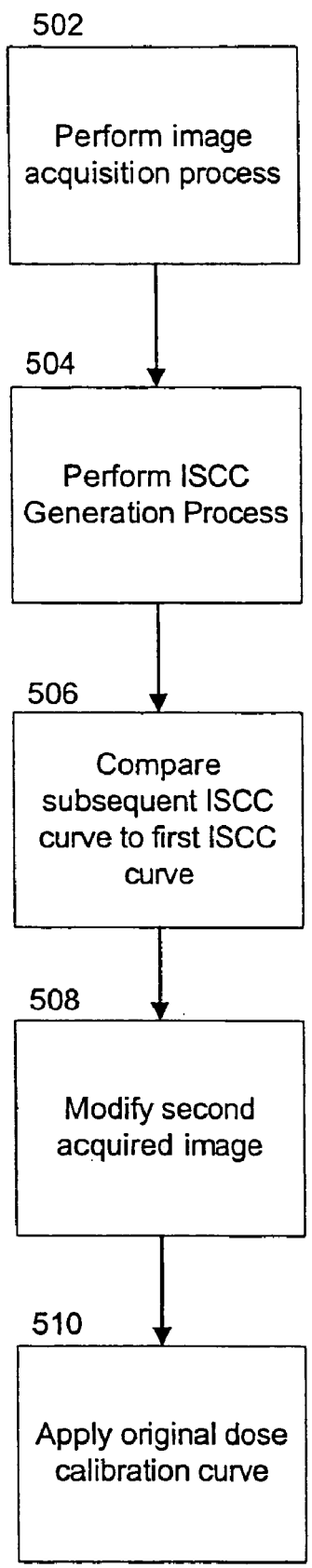
FIG. 5 is a process flow diagram describing a subsequent calibration process.

FIG. 5 describes a subsequent calibration process, i.e., a relative calibration performed for a treatment plan 104b other than the treatment plan 104a for which the calibration curve was developed in step 202 of the initial calibration process described above with reference to FIG. 2. Treatment plan 104b may be referred to as a second or subsequent treatment plan.

In step 502, an image acquisition process is performed with respect to a subsequent treatment plan 104b. Step 502 includes performing the steps described above with reference to FIG. 3A for treatment plan 104b. Accordingly, step 502 produces a dose map 106b and an acquired image 112b.

In step 504, the ISCC generation process described above with reference to FIG. 3B is performed with respect to dose map 106b and acquired image 112b. Accordingly, step 504 produces a subsequent ISCC curve 114b.

In step 506, a comparison is made between the first ISCC curve 114a to the subsequent ISCC curve 114b and identifies differences, or fit, between the two curves. In step 508, the subsequent acquired image 112b is modified based on the differences or fits identified between the first ISCC curve 114a and the subsequent ISCC curve 114b. The objective of this modification is to transform the acquired image 112b to a state in which it can be calibrated using the calibration curve developed in step 202 described above with reference to FIG. 2. The transformation of acquired image 112b may be preformed using a variety of methods known to those skilled in the art including, for example, those discussed in U.S. Pat. No. 6,528,803. The relationship between the two curves, or sets of points, may be as simple as a difference, but could also be more complex and can take the form of look-up tables or curve fits such as will be known to those skilled in the art.

In step 510, calibration curve developed in step 202 described above with reference to FIG. 2 is applied to acquired image 112b.

Evaluation of Experimental Calibration

The ISCC curves developed as described above can advantageously be used to evaluate the usefulness of a calibration curve that is experimentally derived using methods known to those skilled in the art. Accordingly, in some embodiments the ISCC may be compared to an experimentally obtained or calculated calibration curve. The correlation or correspondence between the ISCC and experimentally obtained curves is a measure of the ability of the experimentally derived calibration curve to successfully model a dose distribution such as is represented by a dose map 106 and is shown on an acquired image 112. Those skilled in the art will recognize that it is possible to establish a threshold for acceptance on an experimentally derived calibration curve to prevent curves with excessive errors from being used. The user can also use the correspondence between the ISCC curve and the experimentally derived curve to determine whether discrepancies between dose maps 106 and acquired images 112 are due to calibration errors, TPS modeling errors or radiation delivery errors.

Evaluation and Selection of Normalization Values

The ISCC curves developed as described above further can advantageously be used to evaluate and select normalization values for images, such as acquired images 112 and dose map 106, to be compared for quality assurance purposes. In systems and methods for relative dosimetry such as those newly disclosed herein, it is generally required to normalize the pixel values on the plan and acquired images so that they are scaled over a similar range. The selection of these normalization values can often be difficult. For example, if experimental calibration and ISCC curves differ in shape, then optimizing the normalization at one dose level can compromise agreement at other dose levels. Changing the normalization value on the plan image, i.e., dose map 106, will displace the ISCC curve generated between the normalized plan image and the acquired image 112. Accordingly, the agreement between the ISCC curve and the experientially derived curve can either be optimized over the entire curve or for selected ranges or points of the curve by varying the normalization value. In this manner an optimized normalization value can be achieved for different criteria.

Figure 13:
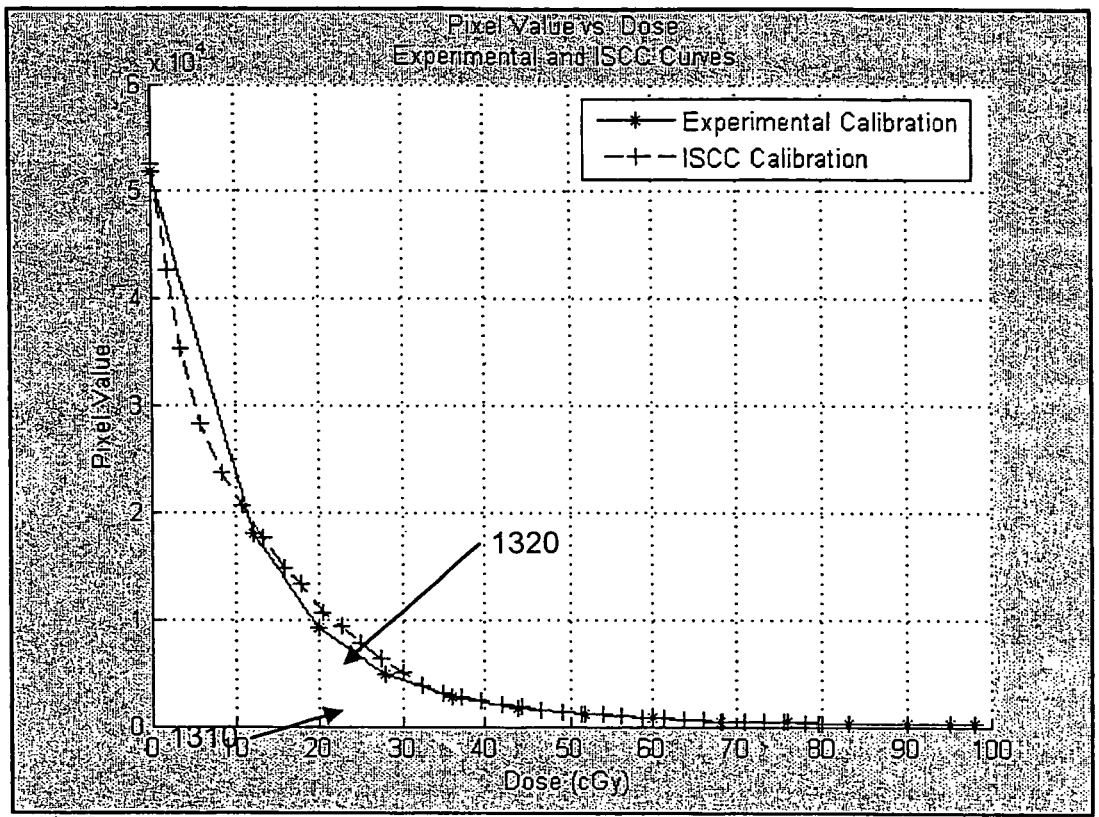
FIG. 13 shows an exemplary graph including an experimentally derived calibration curve and an ISCC curve.

FIG. 13 shows a graph 1300 including an experimentally derived calibration curve 1310, i.e., a calibration curve that was produced in ways known to those skilled in the art or according to the ISCC generation process newly disclosed above. FIG. 13 also shows an ISCC curve 1320 that was produced by dividing a dose map 106 and an acquired image 112 into dose ranges as described above with respect to FIG. 3. There are many ways to compare and normalize curves 1310 and 1320. For example, one way to compare curves 1310 and 1320 is to evaluate the difference between the curves. For purposes of the present example, curves 1310 and 1320 will be evaluated for a selected range of pixel values, generally a common set of pixel values that comprise the common pixel value range of the two curves 1310 and 1320. In this case each pixel value in the selected range will be linearly interpolated, but those skilled in the art will recognize that there are a variety of ways in which this interpolation could be performed.

Figure 14:
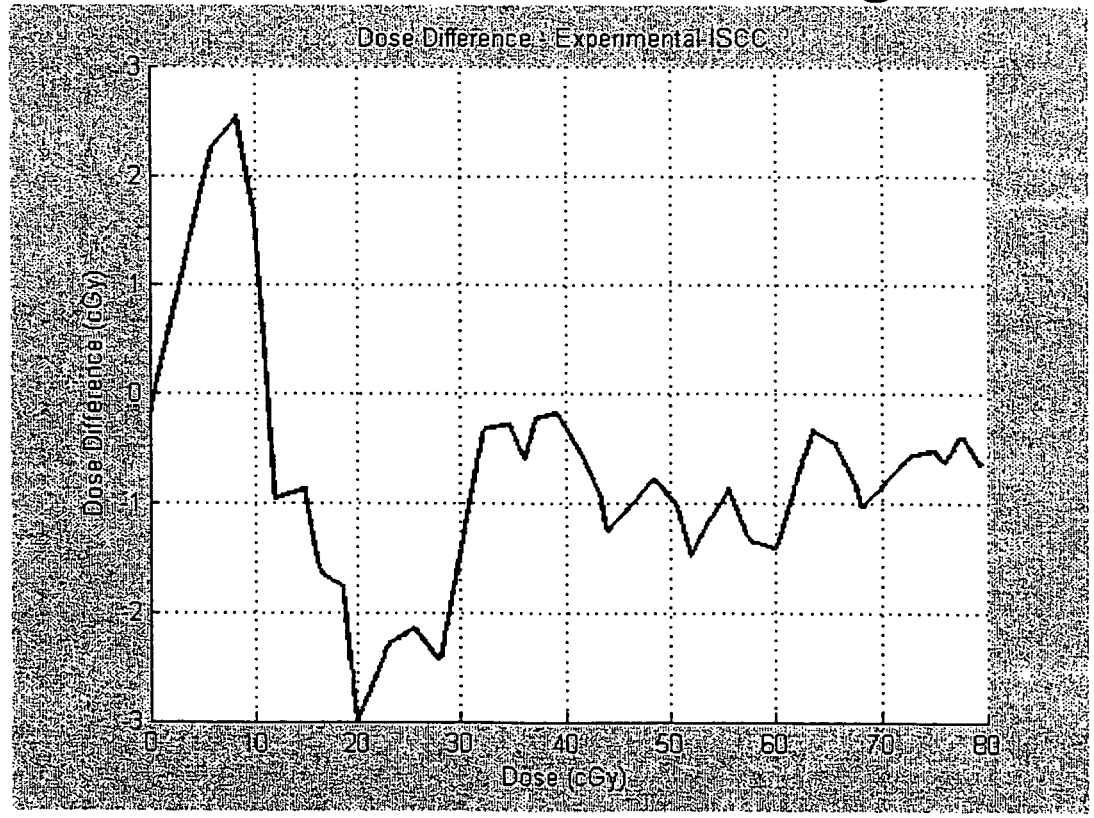
FIG. 14 shows an exemplary graph on which is plotted the dose differences between an experimentally derived calibration curve and an ISCC curve.

Looking at the dose differences between the two curves 1310 and 1320, plotted on graph shown in FIG. 14, one can discern that if one were to use the experimental calibration curve 1310 to calibrate an acquired image 112 from pixel values to dose levels, and then compare that acquired image 112 to a dose map 106 for quality assurance purposes, one would probably see an over-response in the low dose regions (0-10 cGy) of the calibration curve 1310, and an under-response in the 10-30cGy range of the calibration curve 1310. Looking at the plot shown in FIG. 14 in combination with the plot shown in FIG. 13, the observer might conclude that an additional experimental calibration is needed for points in the 0-10 cGy range to better match the ISCC curve 1320. After performing an additional experimental calibration, one could repeat the analysis described with respect to FIGS. 13 and 14 to see if differences between the ISCC curve 1320 and an experimental calibration curve 1310 had improved.

Figure 15A:
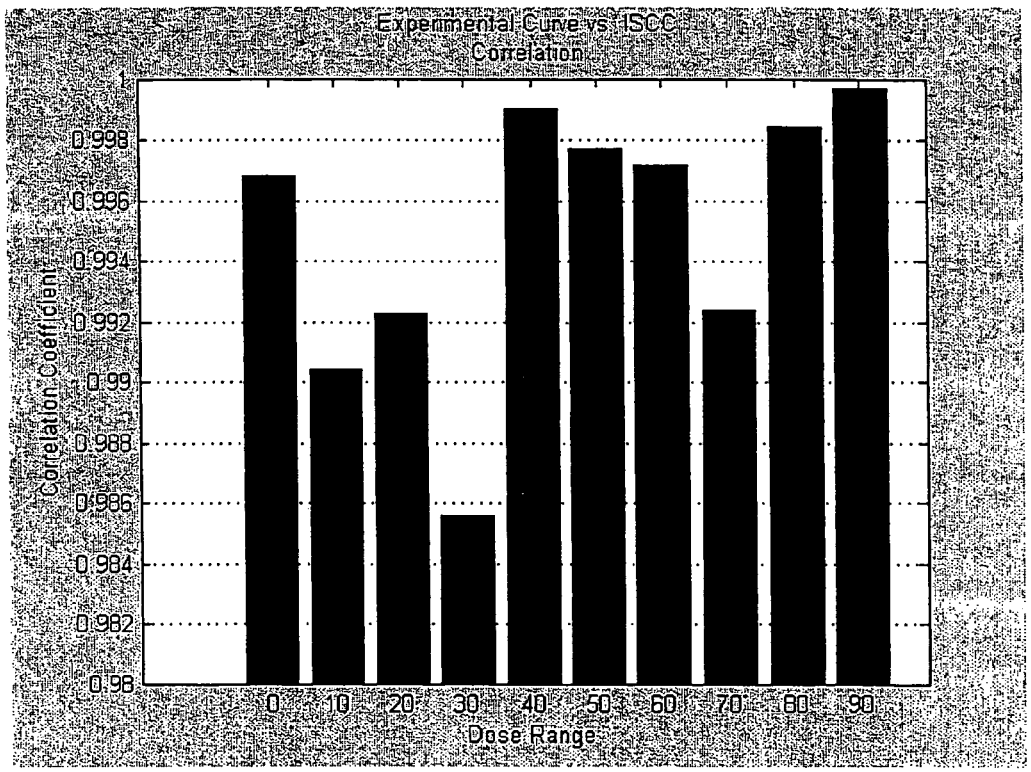
FIG. 15A shows an exemplary plot of a correlation statistic for ten equal sections of a calibration curve.
Figure 15B:
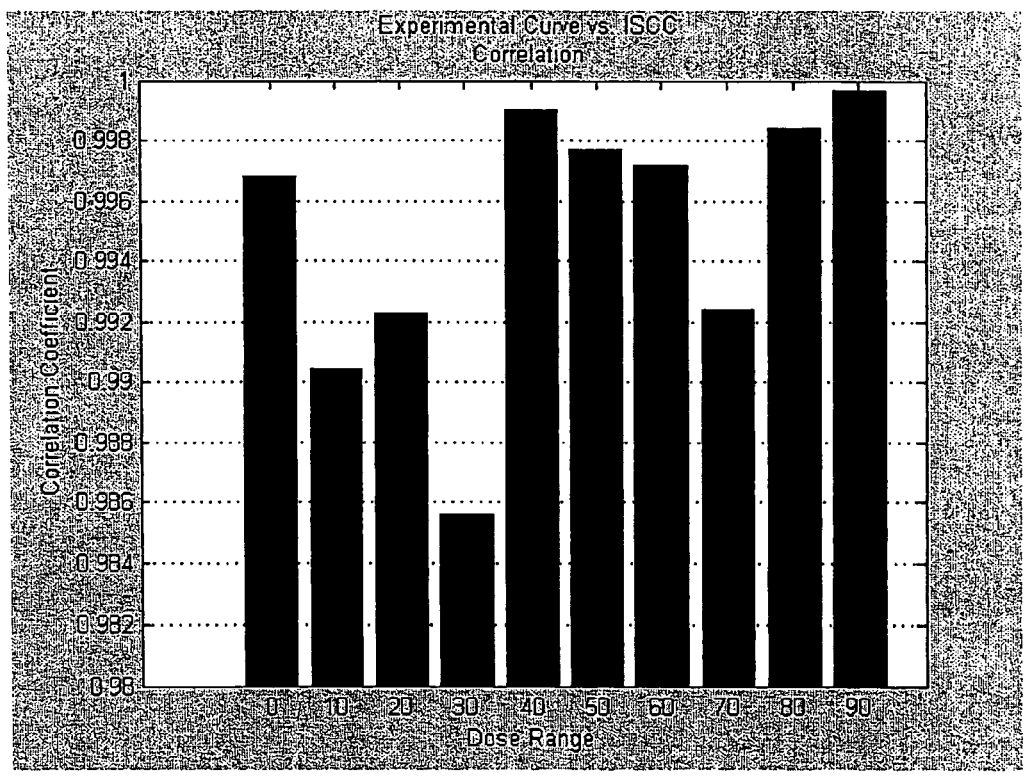
FIG. 15B shows an exemplary plot of a Root Mean Square statistic for ten equal sections of a calibration curve.

It is also possible that, instead of looking at particular dose regions, as is described with respect to FIG. 14, curves 1310 and 1320 could be compared in their entirety. For example, the correlation of the two curves could be evaluated, or the Root Mean Square (RMS) of the difference could be calculated. One could set an acceptance threshold for these parameters in order to accept or reject the experimental curve 1310 for use in calibrating dosimetry devices. Alternatively one could evaluate sections of the curve 1310 individually one were particularly interested in certain regions of the curve (e.g., high dose regions). If curve fitting were being used, this would be called a Spline fit. For example the curve 1310 could be divided into 10 equal sections and statistics, such as a correlation as shown in FIG. 15A or RMS as shown in FIG. 15B, calculated for each.

Figure 16:
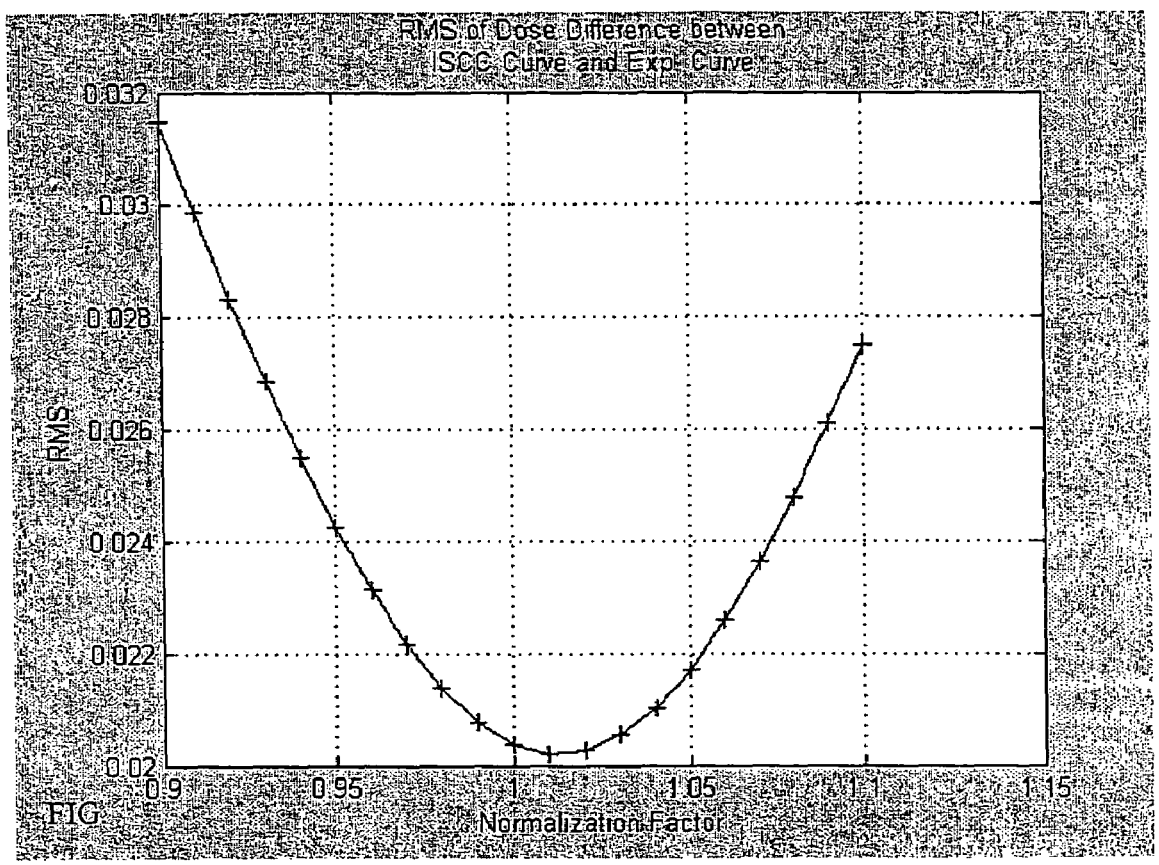
FIG. 16 shows an exemplary normalization curve relating to a portion of a calibration curve.

Further, as mentioned above, a normalization value is often applied to adjust a calibration curve to reduce systemic errors between images being compared, e.g., a dose map 106 and an acquired image 112. For example, one could normalize the ISCC curve 1320 and the experimental curve 1310 to their maximums. The experimental dose curve 1310 may then be adjusted by a range of factors, after which one may plot the RMS of the adjusted experimental curve 1310 against the ISCC curve 1320. Then, by estimating the lowest point on this plot, an optimal normalization factor may be determined. Note that this technique could be performed with respect to a portion of the curve 1310, allowing, for example, optimization for high doses, as is shown in FIG. 16. The lowest point in the curve shown in FIG. 16 appears to be about 1.01, suggesting that 1.01 is an optimal normalization factor for the region shown in FIG. 16. Those skilled in the art will understand that this factor could be further refined by fitting the curve to a polynomial equation.

CONCLUSION

The above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in calibrating dosimetry images, and that the invention will be incorporated into such future embodiments.

We claim:

1. A system for calibrating the dose response of an image acquisition device, comprising:
   means for generating a first self-calibration curve;
   means for generating a second self-calibration curve;
   means for generating an initial calibration; and
   means for performing computations including:

(1) determining at least one difference or fit between the first self-calibration curve and the second self-calibration curve;
(2) modifying an acquired image based on the at least one difference or fit; and
(3) producing a relative calibration based on an application of the initial calibration to the acquired image.

2. The system of claim 1, wherein the initial calibration is related to a first treatment plan and a subsequent calibration is related to a second treatment plan.

3. The system of claim 1, wherein the first self-calibration curve and the second self-calibration curve each relate dosages to the dosage intensities.

4. The system of claim 1, wherein the difference or fit between the first self-calibration curve and the second self-calibration curve is a difference between the first self-calibration curve and the second self-calibration curve.

5. The system of claim 1, wherein the difference or fit is at least one of a lookup table and a curve fit.

6. A method for calibrating the dose response of an image acquisition device, comprising:
    comparing a first self-calibration curve to at least one second self-calibration curve to determine a relationship between the curves;
    modifying an acquired image based on the relationship; and
    applying an initial calibration to the acquired image, whereby the dose response of the image acquisition device is calibrated.

7. The method of claim 6, wherein the at least one second self-calibration curve is one second self-calibration curve and the first self-calibration curve and the initial calibration relate to a first treatment plan, and the second self-calibration curve relates to a second treatment plan.

8. The method of claim 7, wherein the acquired image relates to the second treatment plan.

9. The method of claim 6, wherein the at least one second self-calibration curve is a plurality of second self-calibration curves and the first self-calibration curve and the initial calibration relate to a first treatment plan, and each second self-calibration curve relates to a corresponding one of a plurality of second treatment plans.

10. The method of claim 6, wherein the first self-calibration curve and the second self-calibration curve each relate dosages to the dosage intensities.

11. The method of claim 6, wherein the relationship is one of a difference and a fit.

12. Computer-executable instructions, tangibly embodied on a computer-readable medium, comprising instructions for:
    comparing a first self-calibration curve to at least one second self-calibration curve to determine a relationship between the curves;
    modifying an acquired image based on the relationship; and
    applying an initial calibration to the acquired image, whereby a dose response of an image acquisition device is calibrated.

13. The instructions of claim 12, wherein the at least one second self-calibration curve is one second self-calibration curve, and the first self-calibration curve and the initial calibration relate to a first treatment plan, and the second self-calibration curve relates to a second treatment plan.

14. The instructions of claim 13, wherein the acquired image relates to the second treatment plan.

15. The instructions of claim 12, wherein the at least one second self-calibration curve is a plurality of second self-calibration curves, and the first self-calibration curve and the initial calibration relate to a first treatment plan, and each second self-calibration curve relates to one of a plurality of corresponding second treatment plans.

16. The instructions of claim 12, wherein the first self-calibration curve and the second self-calibration curve each relate dosages to the dosage intensities.

17. The method of claim 12, wherein the relationship is one of a difference and a fit.

* * * * *

UNITED STATES PATENT AND TRADEMARK OFFICE
CERTIFICATE OF CORRECTION

PATENT NO. : 7,639,851 B2  Page 1 of 1
APPLICATION NO. : 11/181057
DATED : December 29, 2009
INVENTOR(S) : Ritt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1202 days.

Signed and Sealed this

Ninth Day of November, 2010

David J. Kappos
*Director of the United States Patent and Trademark Office*